United States Patent
Weiland (10) Patent No.: US 10,507,179 B2
(45) Date of Patent: Dec. 17, 2019

(54) FORMULATIONS OF LEVOSIMENDAN FOR INTRAVENOUS ADMINISTRATION AS INFUSION OR INJECTION AND OF INFUSION CONCENTRATE

(71) Applicant: CARINOPHARM GmbH, Elze (DE)

(72) Inventor: Andrea Weiland, Hohenbrunn (DE)

(73) Assignee: CARINOPHARM GMBH, Elze (DE)

( * ) Notice: Subject to any disclaimer, the term of this patent is extended or adjusted under 35 U.S.C. 154(b) by 0 days.

(21) Appl. No.: 15/772,357

(22) PCT Filed: Nov. 4, 2016

(86) PCT No.: PCT/EP2016/076669
§ 371 (c)(1),
(2) Date: Apr. 30, 2018

(87) PCT Pub. No.: WO2017/077032
PCT Pub. Date: May 11, 2017

(65) Prior Publication Data
US 2018/0318210 A1 Nov. 8, 2018

(30) Foreign Application Priority Data
Nov. 6, 2015 (EP) ..................... 15193521

(51) Int. Cl.
| | | |
|---|---|---|
| A61K 9/00 | (2006.01) | |
| A61K 9/19 | (2006.01) | |
| A61K 31/50 | (2006.01) | |
| A61K 9/08 | (2006.01) | |
| A61K 9/107 | (2006.01) | |
| A61K 9/16 | (2006.01) | |
| A61K 47/10 | (2017.01) | |
| A61K 47/24 | (2006.01) | |
| A61K 47/28 | (2006.01) | |
| A61K 47/34 | (2017.01) | |
| A61K 47/40 | (2006.01) | |
| A61P 9/04 | (2006.01) | |

(52) U.S. Cl.
CPC .............. *A61K 9/0019* (2013.01); *A61K 9/08* (2013.01); *A61K 9/1075* (2013.01); *A61K 9/1617* (2013.01); *A61K 9/1652* (2013.01); *A61K 9/1694* (2013.01); *A61K 9/19* (2013.01); *A61K 31/50* (2013.01); *A61K 47/10* (2013.01); *A61K 47/24* (2013.01); *A61K 47/28* (2013.01); *A61K 47/34* (2013.01); *A61K 47/40* (2013.01); *A61P 9/04* (2018.01)

(58) Field of Classification Search
CPC ........ A61K 31/50; A61K 47/10; A61K 47/24; A61K 47/28; A61K 47/34; A61K 47/40; A61K 9/0019; A61K 9/08; A61K 9/1075; A61K 9/1617; A61K 9/1652; A61K 9/1694; A61K 9/19
See application file for complete search history.

(56) References Cited

U.S. PATENT DOCUMENTS

2008/0104001 A1* 5/2008 Kipp ...................... G06N 3/082
706/25

FOREIGN PATENT DOCUMENTS

| CN | 1470238 A | | 1/2004 | |
|---|---|---|---|---|
| CN | 1611220 A | | 5/2005 | |
| CN | 1626085 A | | 6/2005 | |
| CN | 1689573 A | * | 11/2005 | ............. A61K 31/50 |
| CN | 1689573 A | | 11/2005 | |
| CN | 1839842 A | | 10/2006 | |
| CN | 101411708 A | | 4/2009 | |
| DE | 4207922 A1 | * | 9/1993 | ............... B82Y 5/00 |
| JP | 08048638 A | * | 2/1996 | ............. A61K 45/00 |
| WO | 0119334 A2 | | 3/2001 | |

OTHER PUBLICATIONS

English machine translation of Wang et al. (CN 1689573 A) made Jan. 25, 2019. (Year: 2019).*
English machine translation of Pharmatech GmbH (DE 4207922 A1) made Jan. 25, 2019. (Year: 2019).*
English machine translation of JP-08048638-A made on Mar. 31, 2019. (Year: 2019).*
International Search Report and Written Opinion; PCT/EP2016/076669; dated Jan. 24, 2017; 8 pages.

* cited by examiner

Primary Examiner — Michael B. Pallay
(74) Attorney, Agent, or Firm — Dickinson Wright PLLC (57) ABSTRACT

The present invention relates to improved formulations of Levosimendan for pharmaceutical use, and particularly for intravenous administration as infusion or injection and of infusion concentrates. The present invention therefore relates to pharmaceutical compositions comprising Levosimendan, in which Levosimendan is present in a solubilized form. The formulations have therapeutically and commercial useful concentrations of Levosimendan. The solutions of the invention have enhanced ability at physiological pH (pH 7.4) and are particular useful as infusion or injection solutions or infusion concentrates. The composition according to the present invention can also be spray-dried or lyophilized to obtain a dried powder which is very stable and which powder forms the original solution after reconstitution in water or an aqueous solvent. Levosimendan or (−)-[[4-(1,4,5,6-tetrahydro-4-methyl-6-oxo-3-pyridazi-nyl) phenyl]hydrazono]propanedinitrile is useful in the treatment of congestive heart failure.

25 Claims, 3 Drawing Sheets

FIG. 1

HP-8-CD-Levosimendan fresh alle pH's

FIG 2 after 1 week after 2 weeks

FIG. 3 fresh solution

FIG. 4 after 1 week

FIG. 5 after 2 weeks

FORMULATIONS OF LEVOSIMENDAN FOR INTRAVENOUS ADMINISTRATION AS INFUSION OR INJECTION AND OF INFUSION CONCENTRATE

CROSS-REFERENCE TO RELATED APPLICATIONS

This application is a U.S. National Stage of International Application No. PCT/EP2016/076669, filed on Nov. 4, 2016, which claims the benefit and priority of EP 15 193 521.0 filed Nov. 6, 2015. The entire disclosures of each of the above applications are incorporated herein by reference.

TECHNICAL FIELD

The present invention relates to improved formulations comprising Levosimendan for pharmaceutical use, and particularly to formulations comprising Levosimendan for intravenous administration as infusion or injection solutions or as infusion concentrates. The present invention therefore relates to pharmaceutical compositions comprising Levosimendan in which Levosimendan is present in a solubilized form, and the use of such formulations in the field of medicine. The formulations have therapeutically and commercially useful concentrations of Levosimendan. The solutions of the invention have also enhanced ability at physiological pH (pH 7.4) and are particular useful as infusion or injection solutions or infusion concentrates. The compositions according to the present invention can also be spray-dried or lyophilized to obtain a dried powder which is very stable and which powder forms the original solution after reconstitution in water or another suitable solvent. Levosimendan or (−)-[[4-(1,4,5,6-tetrahydro-4-methyl-6-oxo-3-pyridazi-nyl)phenyl]hydrazono]propane dinitrile is useful in the treatment of congestive heart failure. Therefore, the present invention also relates to the pharmaceutical compositions for use in a method of treating a congestive heart failure or acutely decompensated heart failure (ADHF).

BACKGROUND OF THE INVENTION

Many pharmacological active substances and also Levosimendan and/or its active metabolites OR-1896 and/or OR-1855 (which metabolites are also described in WO 2005/107756) are lipophilic, i.e., only sparingly or negligibly water soluble. The poor water-solubility of Levosimendan results in major difficulties in formulation, particularly when sterile and easily administrable homogenous aqueous solutions are needed. Therefore, the manufacture of Levosimendan solutions involves a number of problems which are caused by the sensitivity of Levosimendan against chemical and physical influences. For example Levosimendan in solutions is sensitive to a chemical degradation which limits the shelf life of solutions and may produce undesirable degradation products.

Levosimendan which is the (−)-enantiomer of [[4-(1,4,5,6-tetrahydro-4-methyl-6-oxo-3-pyridazi-nyl)phenyl]hydrazono]propanedinitrile, and methods for its preparation are described in EP 565546 B1 and WO 97/35841. Levosimendan is potent in the treatment of heart failure and has a significant calcium dependent binding to troponin. Levosimendan is a crystalline powder at room temperature and has a pKa of 6.26. At room temperature the solubility of Levosimendan in phosphate buffer is 0.4 mg/ml at a physiological pH of 7.4. At a pH value of 2 the solubility is as low as 0.02 mg/ml. Levosimendan is not stable in aqueous solutions at physiological pH and is subjected to hydrolytical decomposition. Therefore, Levosimendan is poorly soluble in water and precipitates easily from aqueous solutions. The precipitation of intravenous solutions is extremely dangerous because particulate material may occlude the blood vessels.

The current commercial formulation (Simdax®) (see also EP 1 210 085 B1) is based on the use of anhydrous ethanol and povidone (PVP) as solvents. And anhydrous citric acid is also used to obtain a concentration of 2.5 mg Levosimendan per ml at a pH of approximately 3. According to EP 1 210 085 B1 further solubility enhancing agents also include co-solvents such as propylenglycol, polyalkyleneglycols, e.g. polyethyleneglycol, poloxamers or polyvinylpyrrolidon and linoleic acid or glyceryl monolaurate.

In EP 1 210 085 B1 it was chosen to use an organic solvent approach for chemical stability reason at the pH of approximately 3. However, ethanol is a strong cellular poison and should be avoided in the treatment of humans for several reasons.

CN 1470238 A discloses water based Levosimendan preparations wherein the solubility of Levosimendan in water has been improved by the use of hydroxylpropyl-beta-cyclodextrin.

CN 1839842 A discloses pharmaceutical compositions containing Levosimendan and as solubility enhancing agent solutol HS15 (macrogol-15-hydroxystearate).

CN 1626085 A discloses a process for the preparation of pharmaceutical Levosimendan compositions wherein beta-cyclodextrin, 2-hydroxypropyl-beta-cyclodextrin or 3-hydroxypropyl-beta-cyclodextrin can be used as solubilizer.

CN 101411708 A discloses pharmaceutical compositions containing Levosimendan and hydroxpropyl-beta-cyclodextrin which serves as a solubilizing agent.

CN 1611220 A discloses preparations containing Levosimendan together citric acid, phosphor lipids and 2-hydroxypropyl-beta-cyclodextrin as solubilizing agents.

CN1689573 A discloses Levosimendan-beta-cyclodextrine preparations. Further ethanol and citric acid can be used to get parenteral solutions.

By applying an alternative solubilisation approach it is feasible to obtain a pharmaceutical formulation of Levosimendan at alternative pH values, also at physiological pH.

Levosimendan formulated as described above, i.e. using an organic solvent approach (anhydrous ethanol and/or PVP), can only be diluted with a 5% glucose solution and by using a predefined dilution procedure. Additionally, options for comedication with other drugs in the same i.v. system are very limited. By the present invention the disadvantages of intravenous administration of Levosimendan in ethanol and also the corresponding danger of precipitation when diluting the concentrate in infusion solutions are avoided. Furthermore the solution may advantageously be used at a physiological pH value and the solution may be diluted with different standard infusion solutions.

BRIEF DESCRIPTION OF THE DRAWINGS

Other advantages of the present invention will be readily appreciated, as the same becomes better understood by reference to the following detailed description when considered in connection with the accompanying drawings wherein.

DESCRIPTION OF THE INVENTION

Therefore, it is an object of the present invention to overcome the limited solubility of Levosimendan and to develop pharmaceutical formulations, especially intra venous administration comprising as active ingredient the lipophilic Levosimendan that overcome the limitations of many known approaches and especially of the approach to use organic solvents. It is also an object of the present invention to provide improved formulations of Levosimendan which are chemically and physically stable under prolonged storage and which are suitable for parenteral and in particular intravenous administration. The formulations shall be dilutabel with aqueous infusion solutions at physiological pH values.

The above objects have now been solved in particular by the pharmaceutical composition according to present claim 1 and also by the dried solid product according to claim 11 and the method according to claim 17.

In the dependent claims further preferred embodiments of the invention are disclosed.

Thus in one aspect the invention provides a Levosimendan containing pharmaceutical composition with improved stability, comprising Levosimendan as active ingredient, and a solubilizer selected from the group consisting of cyclodextrins, consisting of sulfo-butyl-ether-beta-cyclodextrin, alpha-cyclodextrin and methylated beta-cyclodextrin and mixtures thereof, fatty acid esters of glycerol, polyethylene derivatives of alpha-tocopherol, bile acids, with the proviso that the use of co-solvents such as ethanol, propyleneglycol, polyethyleneglycol, poloxamers or polyvinylpyrrolidon is excluded.

In another aspect the invention provides a dried powder obtainable from a Levosimendan containing pharmaceutical composition as defined above, wherein the dried powders are obtainable by drying, preferably by freeze-drying or spray-drying or a solution comprising the solubilized Levosimendan, wherein Levosimendan is solubilized by the use of a solubilizer selected from the group consisting of cyclodextrins, consisting of sulfo-butyl-ether-beta-cyclodextrin, alpha-cyclodextrin and methylated beta-cyclodextrins and mixtures thereof, fatty acid esters of glycerol, polyethylene derivatives of alpha-tocopherol, bile acids, or mixtures thereof with the proviso that the use of co-solvents such as ethanol, propyleneglycol, polyethyleneglycol, poloxamers or polyvinylpyrrolidon is excluded. Optionally a suitable pharmaceutical vehicle can be used for freeze-drying for example glycine.

It was surprisingly found, that the formulations/compositions according to present invention can be subjected to spray-drying or freeze-drying whereby powders or solids are obtained, in which preferably a micelle structure or an inclusion compound is obtained. From the said powder or solid, which has properties of acceptable solubility and storage stability, a reconstituted drug solution can be obtained, which rapidly forms a solution again and which regains their original properties in solution. The reconstituted solution is suitable for a parenteral administration, and is in particular suitable for injection or infusion, especially in the form of an initial dose or as an infusion. Preferably the daily dosage of Levosimendan in man is within the range of about 0.1-50 mg, preferably about 0.2-20 mg, depending e.g. on the administration route, age, body weight and condition of the patient. Preferred peak plasma levels of Levosimendan in steady state for the treatment of congestive heart failure are within the range of from about 1 to about 300 ng/ml, more preferably from about 10 to about 150 ng/ml, and especially from about 20 to about 60 ng/ml. Levosimendan can be administered intravenously with the infusion rate in the range of about 0.005-100 μg/kg/min, typically 0.01 to 10 μg/kg/min, more typically about 0.02 to 1 μg/kg/min. For the treatment of heart failure with continuous infusion the suitable rate is preferably 0.05-0.4 μg/kg/min of Levosimendan. Accordingly, it is also an object of the present invention to provide a lyophilized powder for injection or infusion with good solubility, good stability and long time storage.

The present invention overcomes the problem of the poor solubility of Levosimendan, also referred to as the active ingredient in the following, by improving the solubility of Levosimendan in a solvent by adding a third compound or compound mixture, referred to as solubilizer or solubilizing agent in the following. Solubilization as used herein is intended to mean a conversion of a hydrophobic substance, i.e. in the present case the Levosimendan, in water-soluble aggregates under the influence of the solubilizer. According to the present invention co-solvents such as ethanol or propyleneglycole or polyalkyleneglycole e.g. polyethyleneglycol, poloxamers or polyvinylpyrrolidon are not required (see EP 1 210 085 A).

The solubilizer may act inter alia by the formation of complexes, i.e. the active ingredient and the solubilizer form a complex, or by forming micelles, i.e. the active ingredient is incorporated into or entangled to micelles. This kind of solubilisation is also known as micellar solubilisation.

The term active ingredient as used herein is intended to refer to Levosimendan having the following chemical formula as well as its pharmaceutically active metabolites. Pharmaceutically active metabolites are for example the compounds known as OR-1896 and/or OR-1855. OR-1896 is the reaction product of the hydrazone to the corresponding amine, while OR-1855 represents its acylation product (J. A. Segal et al., J. Pharm. Exp. Therap. 325, 331 (2008). OR-1855 and OR-1896 can also be all side chain hydrolyzed degradation products of Levosimendan. It should be noted that the products resulting from hydrolytic degradation during storage (e.g. OR-1420 [mono-hydrolized degradation product]) are not the same as the products of metabolism. OR-1746 is a product formed by oxidation of Levosimendan in an ethanolic solution and refers to (4-Ethoxy-6-imino-5-{[4-(4-methyl-6-oxo-1,4,5,6-tetrahydro-pyridazin-3-yl)-phenyl] hydrazono}-5,6-dihydro-1(H)-pyrimidin-2ylidene)-[4-(4-methyl-6-oxo-1,4,5,6-tetrahydro-pyridazin-3-yl)- phenylazo]acetonitrile and OR-1420 refers to (E)-2-cyano-2-[[4-(1,4,5,6-tetrahydro-4-methyl-6-oxo-3-pyridazinyl)phenyl]hydrazono]acetamide.

According to the invention the following approaches for the solubilization of the active ingredient can be applied:

a) Solubilization by complexation with parenterally suitable cyclodextrins or mixtures of these cyclodextrines: According to the present invention for a parenteral administration the following cyclodextrins are used: sulfo-butyl-ether-beta-cyclodextrin (an anionic cyclodextrin), alpha-cyclodextrin and methylated beta-CD's.

b) Solubilization by micellarization. Micellar solubilisation is a physico-chemical solubilisation technique. Micelles are agglomerates typically having a colloidal dimension. They are formed by amphiphilc compounds, i.e. the solubilizer. Micelles can incorporate lipophilic substances in their core or the lipophilic substance can be entangled at various positions within the micelle walls.

The solubilizer for micellarization can be selected from the group consisting of fatty acid esters of glycerol, polyethylene derivatives of alpha-tocopherol and bile acids. Also within the scope of the present invention are mixtures of one or more of these solubilizers.

For solubilizing the active ingredient by micellarization the following solubilizers may be preferably used: D-alpha tocopheryl polyethylene glycol 1000 succinate, bile salts, e.g. sodium glycocholate, taurocholic acid sodium salt, taurodeoxycholic acid sodium salt, sodium cholate, macrogol glycerol ricino oleate, poly(ethylene oxide)-poly(propylene oxide) block copolymer micelles, mixed micelles composed of soy phosphatidylcholine/sodium glycolate.

c) It is also possible to solubilize Levosimendan by the formation of polymeric micelles and/or hybrid micelles. In this concern in particular the following solubilizers may be used: polyethyleneglycole-polyethylene (PEG2000-PE or PEG5000-PE) or PEG-PCL or PEG-DSPE (distearoyl-PE), PEG-DOPE (dioleyl-PE) (lipid core and a hydrophilic polymer shell) or PEG-PLA (polylactic acid).

d) Solubilization of Levosimendan by the use of sugar based surfactants such as sucrose esters, e.g. sucrose-stearate, -palmitate, -laurate etc.), trehalose-fatty acid esters (as e.g. capryl- and laurylmono esters), nonionic surfactants composed of fatty alcohol polyglycosides, e.g. Plantacare®, and n-octyl-beta-glucopyranoside and other as e.g. n-dodecyl-beta-D-maltopyranoside, is also encompassed by the present invention.

e) Also O/W nanoemulsions respectively parenteral fat emulsion, e.g. emulsions of medium chain triglycerides to solubilize the active ingredient might be prepared, e.g. also by use of soy bean oil, cotton seed oil, safflower oil and other suitable parenterally usable oils emulsified by egg-phosphatidylcholin or soy-phosphatidylcholin.

f) A solubilization through liposomes is also an option encompassed by the present invention. For example dimyristoylphosphatidylcholin (DMPC) or other suitable phosphatidylcholine, either fully saturated or partially unsaturated and respective charge carriers or other detergent additives such as e.g. polysorbates (e.g. 80 or 20), or bile salts (e.g. sodium cholate), as well as PEG-phospholipids (e.g. DSPE-PEG 2000: N-(carbonyl-methoxypolyethyleneglycol 2000)-1,2-distearoyl-sn-glycero-3-phosphoethanolamine and others) as excipient to obtain liposomes may be used.

g) Still further, a solubilization by lipid complexation, e.g. via DMPC/DMPG (dimyristoyl phosphatidyl glycerol) compositions may be applied and is encompassed by the present invention.

h) Still further, a solubilisation through so called solid carriers/hydrophilic carriers is an object and encompassed by the present invention. For example gelucires (polyethyleneglycolglycerides composed of mono- and diesters of polyethyleneglycol) can be used. Especially Gelucirc® 48/16 (PEG-32-stearate [CAS: 9004-99-3]) can be used, wherein Levosimendan is solubilized.

Particular preference is given to solubilization by complexation with cyclodextrins and/or solubilization by micellarization.

The cyclodextrine(s) or any mixture thereof are selected from the group consisting of sulfo-butyl-ether-beta-cyclodextrin, methyl-beta-cyclodextrin, alpha-cyclodextrin (like the product Cavamax W6 Pharma-Alfadex) and mixtures thereof.

The micelles may be formed by the aggregation of only one type of solubilizer, but the formation of hybrid micelles is also within the scope of the present invention. Moreover, polymeric micelles represent a further embodiment of the present invention.

The micelle forming solubilizer may be selected from the solubilizers as specified supra or any mixture thereof. Particularly preferred micelle forming solubilizers are selected from the group consisting of D-alpha tocopheryl polyethylene glycol 1000 succinate, also referred to as TPGS in the following, sodium glycocholate and any mixture thereof.

Using the approaches outlined under a)-h) it is possible to obtain a suitable concentration of Levosimendan also at a pH of 7.4 in an aqueous or aqueous-based formulation, which formulation is suitable for parenteral administration and which can achieve a concentration of 1 to 15 mg active ingredient, i.e. Levosimendan per mL solution. More preferably, the concentration is 2 to 12 mg/mL, still more preferably 2 to 10 mg/mL or 2 to 8 mg/mL. Particularly preferred the concentration is 2.5 mg Levosimendan/mL or higher than 2.5 mg Levosimendan/mL. According to a further embodiment of the present invention the concentration of the active ingredient is 3 mg/mL or higher, preferably 4 mg/mL or higher. By drying the formulation additionally an acceptable stability can be obtained allowing a commercial production and setting an according expiry date. The dried composition can be reconstituted by adding at a time of need a respective amount of a suitable solvent to obtain again the above mentioned concentrations. The reconstituted solution regains its original properties and is suitable for parenteral administration, in particular for injection or infusion.

The pharmaceutical composition according to the present invention may comprise only one type of solubilizer, which may be selected from the solubilizers as specified supra or any combination of the above mentioned solubilizers. The solubilizers are comprised in such amounts that a solubilisation of the active ingredient in the solvent can be achieved.

For compositions comprising one or more cylodextrin(s) as solubilizer the at least one cyclodextrin is preferably present in a mmolar ratio compared to the active ingredient within the range of 1-10 mmol cyclodextrine(s): 1 mmol Levosimendan. Preferably the excess of cyclodextrine(s) is 2-10 mmol cyclodextrine(s): 1 mmol Levosimendan, still more preferably 7-9 mmol cyclodextrine(s): 1 mmol Levosimendan.

For compositions comprising one or more micelle forming solubilizer(s) the at least one micelle forming solubilizer is preferably present in mmolar ratio compared to the active ingredient within the range of 1-50 mmol micelle forming solubilizer(s): 1 mmol Levosimendan. Preferably the excess of cyclodextrine(s) is 2-40 mmol micelle forming solubilizer(s): 1 mmol Levosimendan, still more preferably 4-20 mmol micelle forming solubilizer(s): 1 mmol Levosimendan.

According to another embodiment of the present invention, the solubilizer(s), and in particular the micelle forming solubilzer(s) is/are present in an amount above the critical micelle concentration (CMC) of the respective solubilizer(s). The concentration is preferably at least 0.02 percent by weight, based on the liquid composition. Still more preferably the lower limit is 0.04 percent by weight, preferably 0.08 percent by weight more preferably 2 percent by weight. The upper limit is 45 percent by weight, preferably 20 percent by weight, more preferably 18 percent by weight or 15 percent by weight, again based on the liquid composition.

For D-alpha tocopheryl polyethylene glycol 1000 succinate the critical micelle concentration (CMC) is 0.02 percent by weight. Micelles are typically formed up to a concentration of about 20 percent by weight. Also, for macrogolglycerol ricinooleate the critical micelle concentration (CMC) lies at approximately 0.02 percent by weight.

The pharmaceutical compositions of the present invention can comprise one or more pharmaceutically acceptable excipient(s), which are known in general to the skilled person. The excipient should preferably have good solubility and protect or stabilize the active ingredient under the conditions of low temperature and high vacuum during lyophilization and/or during storage. The excipient may also beneficially effect the structure and elegance of the product and reconstitution ability of the dried product.

Particularly preferred compositions according to the present invention, and in particular those comprising a micelle forming solubilizer or micelles with the incorporated active ingredient, respectively, may comprise at least one cake-forming agent as excipient. Using such cake-forming agents will result in a porous cake or a crystalline or partially crystalline matrix after freeze-drying, which has an improved reconstitution behavior. Also the cake-forming agent will avoid a "fly out" of the active ingredient during the freeze-drying. Particular preference is given to cake-forming agents selected from the group consisting of amino acids, carbohydrates, e.g., monosaccharides, disaccharides, sugar alcohols, oligosaccharides, polysaccharides, peptides, polymeric compounds, salts, and mixtures thereof. Still more preferred are cake-forming agents selected from the group consisting of mannitol, sucrose, maltose, trehalose, glycine, sodium chloride, and mixtures thereof.

In particular sulfo-butyl-ether-beta-cyclodextrin (SBECD), methyl-beta-cyclodextrin and alpha-cyclodextrin may also act as excipient as they are a cyclic sugars as sulfo-butyl-ether-beta-cyclodextrin and methyl-beta-cyclodextrin and alpha-cyclodextrin increase the Tc (Collapse temperature, determined by freeze dry microscopy)/Tg' (determined by differential scanning calorimetry) and therefore allow to freeze dry at elevated temperatures. Also the presence of the above cyclodextrin will result in improved lyophilized cakes and will avoid active pharmaceutical ingredients to "fly out" during the freeze-drying. According to a preferred embodiment of the invention SBECD, alpha-cyclodextrin and methyl-beta-cyclodextrin form 1:1 complexes with Levosimendan. Therefore, it will be possible to dilute endless the respective cyclodextrins/Levosimendan solution with water in every solution for infusion.

The at least one cake-forming agent is preferable present in an amount in a range from 1 to 50 times, preferably 2 to 30 times of the weight of the active ingredient. Glycine and/or mannitol may be comprised in the micellar systems in an amount of 2-15% (w/w), preferably in an amount of 5-10% (w/w). The addition of glycine and/or mannitol results in a dried composition having an improved reconstitution behavior and allowing a fast solution. The dried product is porous and partially crystalline. Trehalose may be also used as cake-forming agent.

The solvent in which the active ingredient is solubilized prior to its drying as well as the solvent used for reconstitution prior to the administration of the pharmaceutical composition may be any solvent suitable for intravenous administration. The solvent may be water, more preferably water for injection (WFI). The solvent may also be an isotonic buffer system. Pharmaceutically acceptable buffer systems are well known in the art. For example the pharmaceutically acceptable buffer system may be selected from the group consisting of citrate, lactate, acetate and phosphate buffers. According to one embodiment of the present invention the pH of the solvent for solubilisation may be adjusted prior to drying the solution. Preferably the solvent for solubilisation may be adjusted to a pH in the range of 4.0 to 8.0, more preferably to a pH of 4.0 to 7.0 and most preferably of about 5.0-6.0, prior to drying the solution. This will help to protect the active ingredient from hydrolytic decomposition during drying, e.g. during the time needed for complete freezing the solution for freeze-drying.

According to one embodiment of the present invention the pH value of the water, in particular the water used for reconstitution, or the pH value of the buffer system, in particular the buffer system used for reconstitution, may be adjusted to a pH value in the range of 7.0 to 8.0, preferably in the range of 7.2 to 7.6, and still more preferably to a pH value of about 7.4. Accordingly an adjustment of the pH value of the solvent to the plasma pH value is possible. For the reconstitution the pH of the then used solvent can preferably be adjusted to a pH in the range of 7.0 to 8.0, more preferably in the range of 7.2 to 7.6, and still more preferably to a pH value of about 7.4 using a suitable buffer. Moreover, the solvent for reconstitution can be selected to provide isotonicity.

According to one embodiment the pharmaceutical composition of the present invention precludes the need of high organic solvent contents. That is the pharmaceutical composition comprises little or no organic solvent such as alcohols. In particular, according to one embodiment the pharmaceutical composition is free of primary alcohols, e.g. ethanol. This applies to the solution prior to drying and/or the reconstituted solution for administration.

A particularly preferred embodiment of the present inventions is a pharmaceutical composition comprising Levosimendan, sulfobutyl ether beta-cyclodextrin (SBECD), and in liquid form water for injection (WFI) or another suitable solvent, such as an infusion solution. The composition may optionally comprise one or more suitable excipient. According to another embodiment the pharmaceutical composition consists of these components. The cyclodextrin is suited to improve the lyophilisation behavior of the pharmaceutical composition as they are cyclic sugars and will provide an elegant cake and avoid the active ingredient "fly out" during the freeze-drying.

Another particularly preferred embodiment of the present inventions is a pharmaceutical composition comprising Levosimendan, D-alpha tocopheryl polyethylene glycol 1000 succinate (TPGS), glycine, and in liquid form water for injection (WFI) or another suitable solvent, such as an infusion solution. The composition may beside glycine optionally comprise one or more suitable excipient(s). According to another embodiment the pharmaceutical composition consists of these components.

Another particularly preferred embodiment of the present inventions is a pharmaceutical composition comprising Levosimendan, sodium glyocholate (SGC), glycine, and in liquid form water for injection (WFI) or another suitable solvent, such as an infusion solution. The composition may beside glycine optionally comprise one or more suitable excipient(s). According to another embodiment the pharmaceutical composition consists of these components.

For all these above particularly preferred embodiments of the present invention the concentration of the active ingredient is 1 to 15 mg active ingredient, i.e. Levosimendan, per mL solution. More preferably, the concentration is 2 to 12 mg/mL, still more preferably 2 to 10 mg/mL or 2 to 8 mg/mL. Particularly preferred the concentration is at least 2.5 mg Levosimendan/mL or higher. According to a further embodiment of the present invention the concentration of the active ingredient is 3 mg/mL or higher, preferably 4 mg/mL or higher. The dried composition can be reconstituted by adding at a time of need a respective amount of a suitable solvent to obtain again the above mentioned concentrations. The reconstituted solution regains its original properties and is suitable for parenteral administration, in particular for injection or infusion.

The sulfo-butyl-ether-beta-cyclodextrin is preferably present in a mmolar ratio compared to the active ingredient within the range of 1-15 mmol cyclodextrine(s): 1 mmol Levosimendan. Preferably the excess of cyclodextrine(s) is 4-12 mmol cyclodextrine(s): 1 mmol Levosimendan, still more preferably 6-10 mmol cyclodextrine(s): 1 mmol Levosimendan.

D-alpha tocopheryl polyethylene glycol 1000 succinate (TPGS) or sodium glyocholate (SGC) is preferably present in mmolar ratio compared to the active ingredient within the range of 1-50 mmol micelle forming solubilizer(s): 1 mmol Levosimendan. Preferably the excess of micelle forming solubilizer(s) is 2-40 mmol micelle forming solubilizer(s): 1 mmol Levosimendan, still more preferably 4-20 mmol micelle forming solubilizer(s): 1 mmol Levosimendan. According to another embodiment, the respective solubilizer is present in an amount above the critical micelle concentration (CMC). The concentration is preferably at least 0.02 percent by weight, based on the liquid composition. Still more preferably the lower limit is 0.04 percent by weight or 0.08 percent by weight or 2 percent by weight. The upper limit is preferably 45 percent by weight, more preferably 20 percent by weight, still more preferably 18 percent by weight or 15 percent by weight, again based on the liquid composition.

If present in the particularly preferred embodiments of the present invention, glycine is preferably comprised in the micellar systems in an amount of 2-15% (w/w), more preferably in an amount of 5-10% (w/w). The presence of glycine will provide an elegant cake during lyophilization and will avoid the active ingredient to "fly out" during the freeze-drying.

These combinations have been shown to be particularly useful, as they provide a good solubilization and reconstitution capacity.

According to another embodiment of the present invention it is also possible to develop mixed micelles build up by two solubilizers forming the micelle. These are for example SPC (soy phosphatidylcholin)/SGC (sodium glyocholate) or SPC/TPGS (D-alpha tocopheryl polyethylene glycol 1000 succinate).

For obtaining a liquid composition with the solubilized Levosimendan the following procedures may preferably be used. From the thus obtained solution the dried pharmaceutical composition can be obtained as will be further detailed below.

As it relates to the inventive embodiment using at least one cyclodextrine as solubilizer a solution of the respective cyclodextrin(s) in a suitable solvent as specified supra, preferably water for injection (WFI) or an isotonic buffer system (e.g. water for injection at pH 7.4 as pH adjustment to plasma is possible), is prepared to which the Levosimendan is added in small portions to obtain the target concentration as specified supra. Upon formation of a clear solution, preferably with the help of a pH adjustment, the solution is aseptically sterile filtered to obtain the liquid for subsequent filling of suitable containers for the subsequent drying.

For obtaining micelles from a process technology point of view there are several manufacturing approaches feasible. According to one approach to the solubilizer present in the solvent, which is e.g. water, the active ingredient is added in small portions. By this the active ingredient is solubilized by interaction with the micelle or micelle forming solubilizers. The thus obtained solution is, after one or more optional sterile filtration step(s), finally dried, preferably freeze-dried. According to another approach a premix (solid dispersion) can be produced by dissolving all components in a suitable organic solvent (ethanol) and then spray-drying said mixture. The thus obtained mix will yield the micelles upon redispersion in a suitable solvent, which maybe water or a pH adjusted water. After one or more optional sterile filtration step(s), the solution can finally be dried, preferably freeze-dried.

According to one embodiment of the present invention micelles solubilisation of Levosimendan is achieved by preparing a solution of the micelle forming solubilizer(s) in a solvent, to which then the active ingredient is added in small portions to obtain the target concentration as specified supra. For example a solution of super refined (peroxide free quality of) macrogol glycerol ricinooleate in water or an isotonic buffer system (e.g. water for injection preferably at pH 7.4) is prepared to which the active ingredient is added in small portions to obtain the target concentration. Upon formation of a clear yellow solution the solution is aseptically sterile filtered to obtain the liquid for subsequent filling of suitable containers for the subsequent drying. Levosimendan has a pKa of 6.3 (weak acid according to Brönstedt). If the pH is adjusted with NaOH to 7.4, a clear yellow solution is obtained. However, if the colour of the solution changes to orange then analysis of the solution shows that degradation products are present (see below: example 5).

According to another embodiment of the present invention a solution of a bile salt, e.g. sodium glycocholate in water or an isotonic buffer system (e.g. water for injection preferably at pH 7.4) is prepared to which the active ingredient is added in small portions to obtain the target concentration as specified supra. Upon formation of a clear yellow-orange solution the solution is aseptically sterile filtered to obtain the liquid for subsequent filling of suitable containers for the subsequent drying.

According to still another embodiment of the present invention a mixed micelle preparation is obtained. For doing so a phosphatidyl cholin (e.g. soybean or egg-phosphatidyl cholin) and a bile salt (e.g. sodium cholate) in a defined molecular ratio, preferably in a ratio of 10:1 to 1:10, more preferably 5:1 to 1:5, are dissolved together with the active ingredient on the target concentration as specified supra in methanol or a suitable other organic solvent or solvent mixture. Upon obtaining a clear solution, the thus obtained solution is then evaporated to dryness by e.g. vacuum (rota vapour, so called film method) to obtain a dry product. The dry film product is then redispersed with a suitable solvent, e.g. water or an isotonic buffer system (e.g. water for injection preferably at pH 7.4) and a clear yellow-orange solution where the active ingredient is solubilized within the mixed micelle is obtained. However, if the color is orange, analysis of the solution shows that degradation products are present.

According to a further embodiment of the present invention a solution of D-alpha-Tocopheryl polyethylene glycol 1000 succinate (VitE-TPGS) in water or an isotonic buffer system (e.g. water for injection preferably at pH 7.4) is prepared by stirring and heating up to approx. 40° C. to obtain a clear aqueous solution to which the Levosimendan is added in small portions to obtain the target concentration. Upon formation of a clear yellow-orange solution the solution is aseptically sterile filtered to obtain the liquid for subsequent filling of suitable containers and for the subsequent drying.

In a further embodiment of the present invention polymeric micelles containing Levosimendan are prepared. They are either prepared as outlined supra for the micellar solubilisation. Alternatively the film method as described above under mixed micelle may be used.

In a further embodiment of the present invention a solubilisation of Levosimendan can be obtained by direct stirring, in this regard we refer to the micellar solubilization under direct stirring.

In a further embodiment of the present invention solubilisation of Levosimendan may simply be achieved by use of commercially available parenteral fat emulsions such as e.g. Lipofundin or Intralipid or other. Levosimendan is pre-dispersed in super refined polysorbate 80 by applying shear force, then this pre-mixture is added to the commercially available parenteral fat emulsion and then subjected to high pressure homogenisation.

In still another embodiment of the present invention the solubilisation of Levosimendan into liposomes is possible by applying the so-called film method by which an organic solution of the liposome forming excipients and Levosimendan on the target concentration is prepared. The solution is then subject of vacuum drying and upon re dispersion of the so obtained film, MLV (multilamellar vesicles) are formed that are subject of subsequent homogenization by standard methods for liposome homogenisation, i.e. high pressure homogenization, extrusion through track-etched polycarbonate etc. Another possibility is the dialysis of mixed micelles that are prepared and then dialysed thus obtaining liposomes by removal of the bile salt.

In still another embodiment of the present invention the solubilisation of Levosimendan may be obtained forming a Levosimendan lipid complex: the preparation is performed as follows the Levosimendan is dissolved in ethanol, sterile filtered and then aseptically added to an aseptically sterile filtered solution of DMPC and DMPG in Dichloromethane. From this solution the DCM is removed by evaporation. The so obtained sterile suspension of Levosimendan is further diluted with the sterile isotonic buffer (e.g. water of injection having a pH of 7.4) and then subject of high pressure homogenization to obtain a suitable parenterally usable nano-suspension.

According to one preferred embodiment of the present invention the liquid formulations of the inventive composition form micelles by which the lipophilic Levosimendan is solubilized. The micelles in the solutions according to the present invention preferably have a diameter of 250 nm or less, especially 5 to 250 nm.

The thus obtained liquid formulations according to the present invention containing the solubilizied Levosimendan can also be subjected to a drying process for obtaining a powder or solid suitable for injection or infusion having good solubility, good stability and long storage period (see tables 1 to 3 below).

A further embodiment of the present invention is therefore, a dried powder or solid comprising Levosimendan and at least one solubilizer as identified above, wherein the Levosimendan is present in a solubilized form. The dried pharmaceutical composition can be obtained by drying the above mentioned solutions comprising the solubilized active ingredient. The dried pharmaceutical composition is the storage form which is suitable for reconstitution prior to administration.

A method for preparing such a dried powder or solid comprises the steps of (i) providing a solution of the at least one solubilizer in a solvent, (ii) adding the Levosimendan into that solution, (iii) sterilization, preferably sterile filtration, of the thus obtained solution, (iv) optionally split charging the sterilized solution, and (v) drying, preferably freeze-drying or spray-drying, the sterilized solution.

These steps (i) to (iv) may be performed as specified supra. According to one embodiment prior to the drying, preferably the freeze-drying or spray-drying, the pH of the solution to be dried can be adjusted preferably to a pH in the range of 4.0 to 8.0, more preferably in the range of 4.0 to 7.0 and most preferably of about 5.0-6.0. The adjustment can be performed after step number (ii) but before step (iii) for example. This will help to protect the active ingredient from hydrolytic decomposition while drying, e.g. during the time needed for complete freezing the solution for subsequent freeze-drying. For adjusting the pH preferably acetic acid is used, because of its low volatility. The drying may be achieved by spray-drying or freeze-drying. For the reconstitution the pH can then be adjusted to a pH in the range of 7.0 to 8.0.

Spray-drying and freeze-drying processes are in general known to the skilled person, and various conventional types of spray-drying and freeze drying are adequately described in the state of the art, e.g. in relevant text books.

In general freeze-drying processes comprise three stages, namely freezing, primary drying and secondary drying. During freezing the solution to be dried is converted into a solid state. The freezing is performed below a critical temperature which is the collapse temperature (Tc) for amorphous products. The freezing may also comprise at least one annealing step. During the primary drying the frozen solvent is sublimated under reduced pressure, resulting in a dry, structurally intact product. The primary drying is performed by controlling the shelf temperature (Ts) and the chamber pressure (Pc). The secondary drying is performed to remove residual moisture still bound to the product after the primary drying. The residual moisture content may be as high as 7-8%. The secondary drying is performed at a higher shelf temperature to reduce the residual moisture content, which is preferably below 3%.

It has been shown for the micellar systems that in the dried powder the micelle structure is maintained. The powder can then be stored in containers and can be reconstituted with an aqueous solution, preferably having a pH in the range of 7.2 to 7.6, or simply with water for injection. In this aqueous solution it will be possible to add further additives like buffers and other usual pharmaceutical excipients. In particular, if according to one embodiment of the present invention an acid for adjusting the pH in the range of 4.0 to 6.0 prior to drying is used, as explained supra, for the reconstitution the pH of the then used solvent can preferably be adjusted to a pH in the range of 5.0 to 8.0, more preferably in the range of 7.2 to 7.6, and still more preferably to a pH value of about 7.4 using a suitable buffer.

The reconstitution of the pharmaceutical composition may be achieved by adding a solvent in such an amount that a concentrate for injection as achieved. In that concentrate the active ingredient is comprised in an amount of 1 to 15 mg active ingredient, i.e. Levosimendan, per mL concentrate. More preferably, the concentration is 2 to 12 mg/mL, still more preferably 2 to 10 mg/mL or 2 to 8 mg/mL. Particularly preferred the concentration is at least 2.5 mg Levosimendan/mL or higher. According to a further embodiment of the present invention the concentration of the active ingredient is 3 mg/mL or higher, preferably 4 mg/mL or higher. Prior to administration the concentrate may be further diluted into a standard infusion solution.

Alternatively the dried powder or solid may be diluted by adding a suitable solvent, for example a standard infusion solution, to directly obtain an infusion solution for administration. In this case the suitable solvent should preferably have a pH value in the range of 7.2 to 7.6, more preferably about 7.4. Isotonicity of the solvent is needed and can for example be provided by the solvent.

Advantageously the dried pharmaceutical product of the present invention can be reconstituted with a solvent having a pH value close to or being the physiological pH. The solvent can be chosen to be of high pharmaceutical acceptance. That is on particular the use of organic solvents, such as ethanol, can be avoided. Patient compliance can be improved and side effects can be reduced.

In a further aspect the present invention therefore relates to the above described pharmaceutical composition for use as a medicament. Still more preferably the pharmaceutical composition is for use in a method of treating a congestive heart failure or acutely decompensated heart failure (ADHF).

Preferably the pharmaceutical composition is present as a dried powder, still more preferred in lyophilized form, and is reconstituted before administration by adding a suitable solvent as specified supra. That is the present invention also relates to the above described dried powder for use as a medicament, preferably for use in a method of treating congestive heart failure (AHF) or acutely decompensated heart failure (ADHF).

The reconstitution is preferably performed ideally at or close to the intended time of administration in order to avoid any contaminations with microbes. The skilled person is familiar with the handling of pharmaceutical compositions for reconstitution and reconstituted solutions.

For administration the pharmaceutical composition may be reconstituted to a solution suitable for intravenous administration, which solution is in particular a concentrate for injection or an infusion solution or an injection solution. The infusion concentrate comprises the Levosimendan in an amount of 1 to 15 mg/ml solution, preferably 2.5 mg/ml solution. The concentrate can be used as an initial dose, preferably by infusion, or for a continuous infusion (perfusion with certain infusion rate). It is dosed by kg of body weight and hepatic function.

The solvent for reconstitution may be water, preferably water having pH in the range of 7.2 to 7.6, or may be an isotonic buffer system, preferably an isotonic buffer system having a pH in the range of 7.2 to 7.6. The solvent used for reconstitution can be such that isotonicity and a physiologically acceptable pH can be achieved.

The invention will now be further described by the following examples.

Example 1

Vitamin E-TPGS as Solubilizer

Using Celine[3D], a Vitamin E TPGS-based drug formulation is investigated. Of particular interest are the micellar characteristics and effects of the freeze/thaw homogenization cycle. The following properties of the micelles were determined:
  Morphology and shape properties (volume, area, major radii)
  Statistical distribution of the shape properties of the micelles
  Description of an aggregation of the micelles
  Distribution of the micelles in the sample
  Measured Samples
  Two samples of Vitamin E TPGS (20% (m/m) formulation in isotonic phosphate buffer pH 7.4 were supplied:
    Formulation, 1 mL, 10 mg/mL Levosimendan in the formulation
    Control, 1 mL, without active pharmaceutical ingredient
    Brief Summary of the Results The formulation and control sample exhibited almost identical behaviour. Measured micelle size and general micelle distribution was identical in both of them. Micelle size distribution was relatively wide in the range of 6.5-8.0 nm with the formulation sample exhibiting additional peak at 9.3 nm. Statistics on the size of the micelles were provided and matched the expected values well.

3D reconstruction was not possible due to the irregular nature of the monomer aggregates.

Example 2 a) Sulfo-Butyl-Ether-Beta-Cyclodextrin (SBECD)
  Formulation:
Levosimendan: 250 mg
Sulfo-butyl-ether-beta-cyclodextrin (SBECD): 17.5 g
NaOH q.s. or e.g. acetic acid for pH adjustment
Water for injection (WFI): ad 100 ml
  Procedure:
The sulfo-butyl-ether-beta-cyclodextrin (SBECD) is dissolved in water for injection (WFI), upon formation of a solution the Levosimendan is added in small portions into the stirred solution of SBECD/water. The pH is then adjusted to a suitable pH (see above). The thus obtained solution is sterile filtered via a 0.22 µm filter. Per vial 5 mL of the filtered solution is added and then lyophilized.

For freeze-drying the temperature of the shelfes (Ts) is decreased to −5° C. and the filled vials are placed into the freeze drying chamber of the freeze-drying device (SMART Lyostar II); for freezing. After freezing at −40° C. the Ts is increased to −15° C. to perform an annealing step at −15° C. to obtain bigger ice crystals using the ostwald ripening. After the annealing the shelf temperature is again reduced to −40° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to 5° C., and kept there until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 8 hours to obtain the target residual moisture of equal or below 3% (w/w) of water.

Properties:

The properties of the resulted product are follows: Good appearance of the cake, easy to dissolve in water, with a reconstitution time of <2 min, the so obtained solution is a clear yellowish solution. The pH of the solution is. can then be adjusted to a suitable pH (see above).

b) Alpha-Cyclodextrin (α-CD)

Formulation:
Levosimendan: 250 mg
alpha-cyclodextrin (α-CD): 9.73 g
NaOH q.s. or acetic acid for pH adjustment
Water for injection (WFI): ad 100 ml Procedure:

The alpha-cyclodextrin (α-CD) is dissolved in water for injection (WFI), upon formation of a solution the Levosimendan is added in small portions into the stirred solution of (α-CD)/water. The pH is adjusted to a suitable pH (see above). The thus obtained solution is sterile filtered via a 0.22 µm filter. Per vial 5 mL of the filtered solution is added and then lyophilized.

For freeze-drying the temperature of the shelfes (Ts) is decreased to −5° C. and the filled vials are placed into the freeze drying chamber of the freeze-drying device (SMART Lyostar II); for freezing. After freezing at −40° C. the Ts is increased to −15° C. to perform an annealing step at −15° C. to obtain bigger ice crystals using the ostwald ripening. After the annealing the shelf temperature is again reduced to −40° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to 5° C., and kept there until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 8 hours to obtain the target residual moisture of equal or below 3% (w/w) of water.

Properties:

The properties of the resulted product are follows: Good appearance of the cake, easy to dissolve in water, with a reconstitution time of <2 min, the so obtained solution is a clear yellowish solution. The pH of the solution can then be adjusted to a suitable pH (see above).

c) Methyl-Beta-Cyclodextrin (MβCD)

Formulation:
Levosimendan: 250 mg
Methyl-beta-cyclodextrin (MβCD): 5.4 g
NaOH q.s. or acetic acid for pH adjustment
Water for injection (WFI): ad 100 ml Procedure:

The methyl-beta-cyclodextrin (MβCD) is dissolved in water for injection (WFI), upon formation of a solution the Levosimendan is added in small portions into the stirred solution of MβCD/water. The pH is adjusted to a suitable pH. The thus obtained solution is sterile filtered via a 0.22 µm filter. Per vial 5 ml of the filtered solution is added and then lyophilized.

For freeze-drying the temperature of the shelfes (Ts) is decreased to −5° C. and the filled vials are placed into the freeze drying chamber of the freeze-drying device (SMART Lyostar II); for freezing. After freezing at −40° C. the Ts is increased to −15° C. to perform an annealing step at −15° C. to obtain bigger ice crystals using the ostwald ripening. After the annealing the shelf temperature is again reduced to −40° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to 5° C., and kept there until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 8 hours to obtain the target residual moisture of equal or below 3% (w/w) of water.

Properties:

The properties of the resulted product are follows: Good appearance of the cake, easy to dissolve in water, with a reconstitution time of <2 min, the so obtained solution is a clear yellowish solution. The pH of the solution can then be adjusted to a suitable pH (see above).

d) Hydroxypropyl-Beta-Cyclodextrin (HP-β-CD) (Prior Art)

Formulation:
Levosimendan: 250 mg
Hydroxypropyl-beta-cyclodextrin (HP-β-CD): 17.5 g
NaOH q.s. or acetic acid for pH adjustment
Water for injection (WFI): ad 100 ml Procedure:

The hydroxypropyl-beta-cyclodextrin (HP-β-CD) is dissolved in water for injection (WFI), upon formation of a solution the Levosimendan is added in small portions into the stirred solution of HP-β-CD/water. The pH is adjusted to a suitable pH. The thus obtained solution is sterile filtered via a 0.22 µm filter. Per vial 5 mL of the filtered solution is added and then lyophilized.

For freeze-drying the temperature of the shelfes (Ts) is decreased to −5° C. and the filled vials are placed into the freeze drying chamber of the freeze-drying device (SMART Lyostar II); for freezing. After freezing at −40° C. the Ts is increased to −15° C. to perform an annealing step at −15° C. to obtain bigger ice crystals using the ostwald ripening. After the annealing the shelf temperature is again reduced to −40° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to 5° C., and kept there until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 8 hours to obtain the target residual moisture of equal or below 3% (w/w) of water.

Properties:

Good appearance of the cake, easy to dissolve in water. After storage (2 weeks) deepening of the yellow colour to orange occurred. Degradation products of Levosimendan are detectable. At lower pH values (pH 6.0) degradation products appear.

Example 3

Formulation:
Levosimendan: 250 mg
10% (w/w) TPGS in water for injection: 10 g
Glycine: 5 g
Water for injection (WFI): ad 100 ml Procedure:

First the glycine and then the TPGS is dissolved in water for injection (WFI), upon formation of a solution the Levosimendan is added in small portions into the stirred solution of Glycin/TPGS/water. The thus obtained solution is sterile filtered via a 0.22 μm filter. Per vial 5 mL of the filtered solution is added and then lyophilized.

For freeze-drying the temperature of the shelfes (Ts) is decreased to −50° C. and the filled vials were placed into the freeze drying chamber of the freeze-drying device (SMART Lyostar III; for freezing. After freezing at −50° C. the Ts is increased to −20° C. to perform an annealing step at −20° C. to obtain bigger ice crystals using the ostwald ripening and the crystallization of the lyo excipient (glycine) occurs. After the annealing the shelf temperature is again reduced to −50° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to −10° C., and kept for some hours, after a while the Ts is ramped to −5° C. and then to 10° C. until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 15 hours to obtain the target residual moisture of equal or below 1% (w/w) of water.

Properties:

The properties of the resulted product are follows: Good appearance of the cake, easy to dissolve in water.

Example 4

Formulation:
Levosimendan: 250 mg
5% (w/w) sodium glyocholate (SGC) in water for injection: 5 g
Glycine: 5 g
Water for injection (WFI): ad 100 ml Procedure:

First the glycine and then the SGC is dissolved in water for injection (WFI), upon formation of a solution the Levosimendan is added in small portions into the stirred solution of glycine/SGC/water. The thus obtained solution is sterile filtered via a 0.22 μm filter. Per vial 5 mL of the filtered solution is added and then lyophilize. No pH adjustment is done.

For freeze-drying the temperature of the shelfes (Ts) is decreased to −50° C. and the filled vials were placed into the freeze drying chamber of the freeze-drying device (SMART Lyostar III; for freezing. After freezing at −50° C. the Ts is increased to −20° C. to perform an annealing step at −20° C. to obtain bigger ice crystals using the ostwald ripening and the crystallization of the lyo excipient (glycine) occurs. After the annealing the shelf temperature is again reduced to −50° C. to ensure complete ice solidification.

For the primary drying (which means the ice crystals are directly transferred into water vapour gas) a vacuum of approx. 0.09 mbar or other suitable vacuum range (e.g. 60 mTorr) is applied then the shelf temperature (Ts) is increased to −10° C., and kept for some hours, after a while the Ts is ramped to −5° C. and then to 10° C. until the end of the primary drying which can be detected by several means, i.e. by the merging of the pirani gauge pressure device with the capacitance manometer gauge or by measuring the Tp (product temperature) in the vials in the critical positions ("cold spot" by wireless temperature measurement e.g. TEMPRIS® or Thermocouples). For the secondary drying the temperature (Ts) is again increased to 40° C. and the samples are dried for additional e.g. 15 hours to obtain the target residual moisture of equal or not more than 2% (w/w) of water.

Properties:

The properties of the resulted product are follows: Good appearance of the cake, easy to dissolve in water.

Example 5

The effect of the stability studies of Levosimendan/SBECD complexes (solubile inclusion, 1:1 complexes) in comparison to hydroxylpropyl-beta-cyclodextrin (HP-beta-CD)/Levosimendan complexes (1:1 complexes) according to the prior art at different temperatures up to three months was tested (table 1 and 2 further below).

Figure 1:
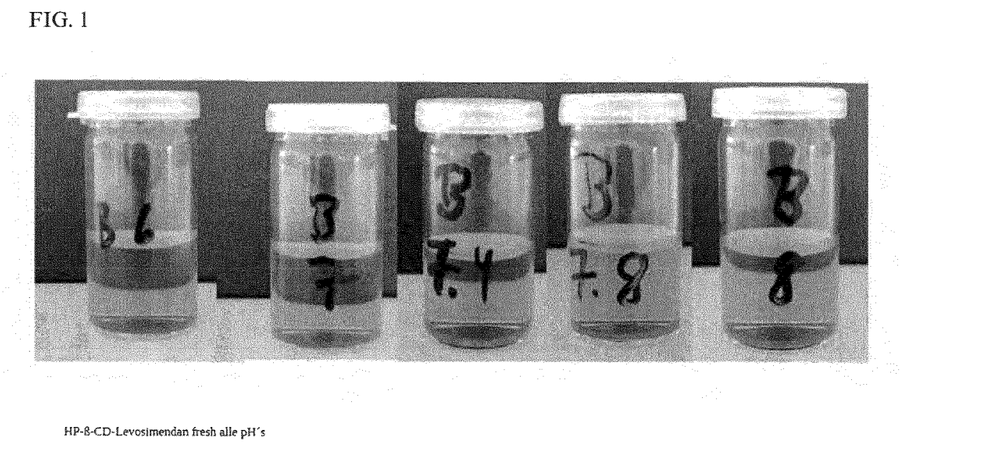
FIGS. 1 to 2 illustrate pictures of stabilizer solutions of Levosimendan/HP-beta-CD complexes at different pH-values and different times.
Figure 2:
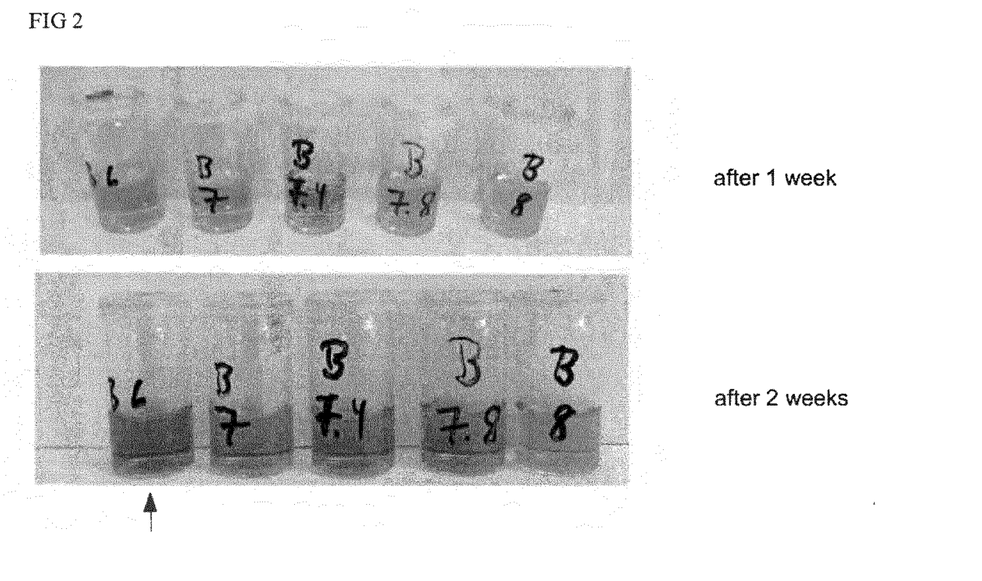

FIGS. 1 and 2 show pictures of stabilizer of solutions of Levosimendan/HP-beta-CD complexes at different pH-values and different times.

Figure 3:
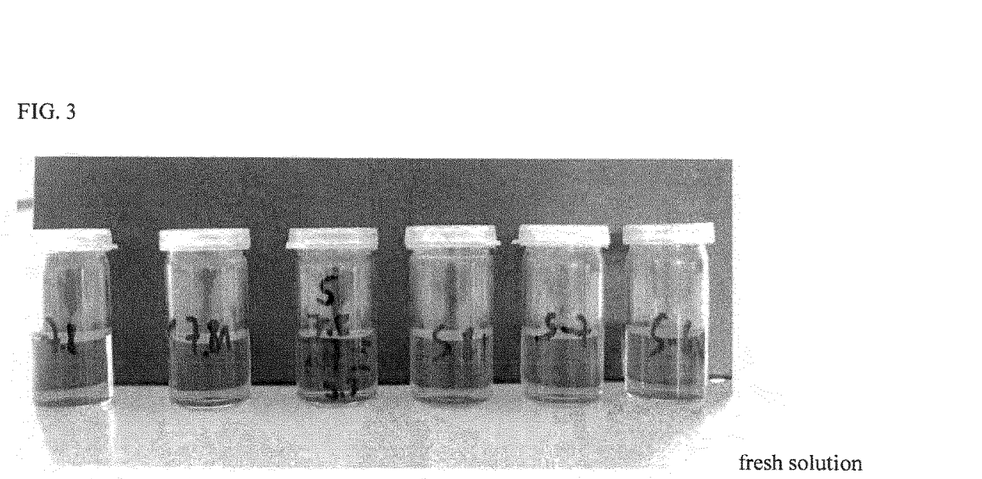
FIGS. 3 to 5 illustrate pictures of stabilizer solutions of Levosimendan/SBECD-complexes at different pH values and different times.
Figure 4:
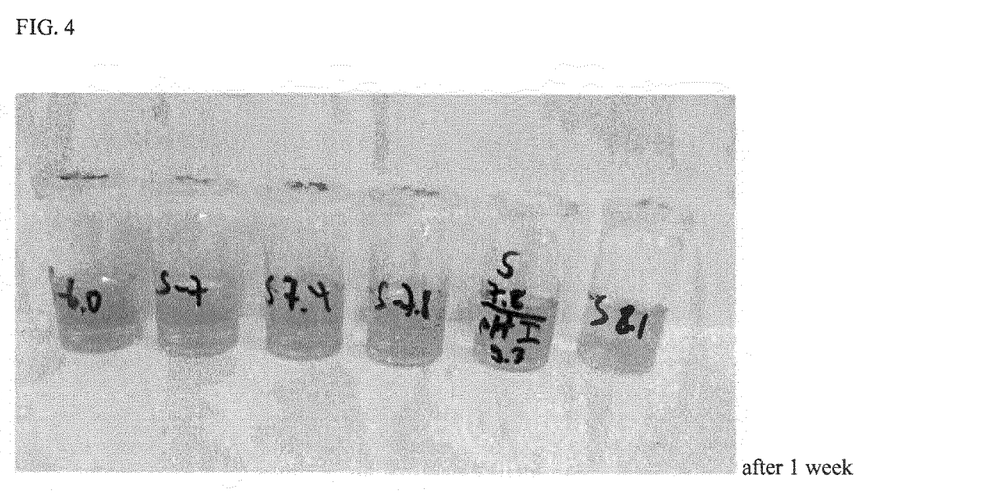
Figure 5:
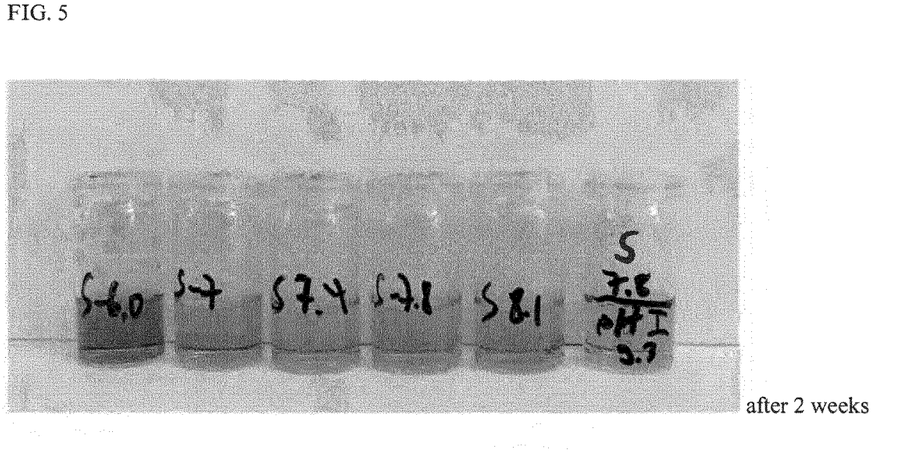

FIGS. 3-5 show pictures of stabilizer solutions of Levosimendan/SBECD-complexes at different pH values and different times.

The results show that at physiological pH the lyo-formulation with SBECD is much more stable than that of HP-beta-CD (see below tables 1, 2 and 3).

The chemical stability of Levosimendan formulations were tested by mirroring the degradation product OR-1420 by the help of HPLC. The Levosimendan formulations were stored at 2-8° C. and 40° C./75% r.h. over a period of up to 3 months. In the following analytics applied are given:

Assay Methods
Equipment, Analytical Parameter and Software
Sample Preparation, Dilution, Sample Vial White-glass measuring flasks, white-glass snap cap vials, Eppendorf/Brand volumetric micro pipettes (air cushion), graduated glass pipettes, UPLC vials.

Chemicals
Formic Acid UPLC-Grade
Acetonitril UPLC-Grade
H20 UPLC-Grade
Methanol UPLC-Grade
Ampuwa
Levosimendan
Acquity UPLC CSH C18 1.7 μm 2.1×50 mm

| LC-INSTRUMENT | Acquity UPLC Co. Waters |
| --- | --- |
| Software (Version) | Empower 3 |
| UV-Detector | PDA Detector Co. Water |
| Column | Acquity UPLC CSH C18 1.7 μm 2.1 × 50 mm |
| Injection volume | 1 μL |
| Flow rate | 0.5 mL/min |
| Isocratic | A: $H_2O$ 0.2% formid acid |
| | B: acetonitril |

| | % A | % B |
| --- | --- | --- |
| | 60 | 40 |

| Column temperature | 35° C. |
| --- | --- |
| Autosampler temperature | 10° C. |
| Wavelength | 210-400 nm (248 nm) |
| Run Time | 3 min |
| GC-time | 70 min |

Purity Methods
Equipment, Analytical Parameter and Software
Sample Preparation, Dilution, Sample Vial White-glass measuring flasks, white-glass snap cap vials, Eppendorf/Brand volumetric micro pipettes (air cushion), graduated glass pipettes, UPLC vials.

Chemicals
Formic Acid UPLC-Grade
Acetonitril UPLC-Grade
H20 UPLC-Grade
Methanol UPLC-Grade
Ampuwa
Levosimendan
DBTA
Acquity UPLC CSH C18 1.7 μm 2.1×50 mm

| LC-INSTRUMENT | Acquity UPLC Co. Waters |
| --- | --- |
| Software (Version) | Empower 3 |
| UV-Detector | PDA Detector Co. Water |
| Column | Acquity UPLC CSH C18 1.7 μm 2.1 × 50 mm |
| Injection volume | 1 μL |
| Flow rate | 0.6 mL/min |
| Gradient | A: $H_2O$ 0.2% formic acid |
| | B: acetonitril |

| Time min. | % A | % B |
| --- | --- | --- |
| 0 | 90 | 10 |
| 0.80 | 90 | 10 |
| 2.50 | 5 | 95 |
| 3.30 | 5 | 95 |
| 3.50 | 90 | 10 |
| 4.00 | 90 | 10 |

| Column temperature | 60° C. |
| --- | --- |
| Autosampler temperature | 10° C. |
| Wavelength | 210-400 nm (248 nm) |
| Run Time | 4 min |
| Solvent mixture | Methanol/Acetonitrile/Water 20/40/40 V/V/V |

TABLE 1

(solutions stored at 2-8° C.)
aqueous (liquid) solubility stability HpßCD-versus SBECD

| | samples manufactured | HpßCD | SBECD | HpßCD | SBECD | HpßCD | SBECD | HpßCD | SBECD | HpßCD | SBECD | SBECD |
| --- | --- | --- | --- | --- | --- | --- | --- | --- | --- | --- | --- | --- |
| | target pH | pH 6.0 | pH 6.0 | pH 7.0 | pH 7.0 | pH 7.4 | pH 7.4 | pH 7.8 | pH 7.8 | pH 8.0 | pH 8.0 | pH 9.3 |
| | weighing in mg | | | | | | | | | | | |
| 1 | Levosimendan Lot: 460010714 | 12.66 | 12.45 | 12.68 | 12.61 | 12.6 | 12.51 | 12.6 | 12.48 | 12.68 | 12.63 | 12.39 |
| 2 | HP Beta W7HP7 Lot: A1411A0050 or SBECD Lot: 151101, respectively | 1020.56 | 1060.76 | 1019.95 | 1061.07 | 893.29 | 928.09 | 893.14 | 926.64 | 893.14 | 928.78 | 927.05 |
| 3 | WFI ad mL | 5 | 5 | 5 | 5 | 5 | 5 | 5 | 5 | 5 | 5 | 5 |
| 4 | Final pH | 6.0 | 5.93 | 7.08 | 7 | 7.4 | 7.33 | 7.8 | 7.8 | 8.0 | 8.1 | 9.3 |
| 5 | Assay mg/mL | 2.31 | 2.42 | 2.31 | 2.37 | 2.43 | 2.49 | 2.44 | 2.43 | 2.44 | 2.4 | 2.43 |
| 6 | Impurity μg/mL | | | | | | | | | | | |
| | RRT 0.81 | 4.68/17.8 | n.d./8.56 | 2.51/14.4 | n.d./10.8 | 3.25/14.5 | n.d./14.0 | 2.72/15.2 | n.d./14.9 | 2.43/14.5 | n.d/15.1 | 2.47/16.0 |
| | RRT 0.95 | 4.47/13.0 | 4.49/19.0 | n.d./n.d. | n.d./n.d. | n.d./n.d. | n.d./n.d. | n.d./n.d. | n.d./n.d. | n.d./n.d. | n.d./n.d. | n.d./n.d. |
| 7 | pH at assay | 6.2 | 6.1 | 7.3 | 7.1 | 7.5 | 7.4 | 8.0 | 7.7 | 8.1 | 7.9 | 9.4 |

PH 6.0 and 7.0: 200 mg/mL of the respective cyclodextrin
PH 7.4, pH. 7.8 and pH 8.0: 175 mg/mL of the respective cyclodextrin
RRT 0.81   OR-1420   monohydrolyzed   m/z = 299 (M + 1) Mono-hydrolized impurity
                     impurity
RRT 0.95           not known
Manufacture 21.4.2016
purity measured 2 times   1st measurement: 26.04.2016 (5 days)-2nd measurement 10.5.2016 (20 days)
interpretation:
1)           SBECD provides a better stabilisation compared to HpßCD as can be taken from the figures at each pH
2)           the optimal pH is between 7.0-8.0
3)           at pH 6 and pH 9.3 there is increased hydrolytic cleavage

TABLE 2

(lyoproduct stored at 25° C.)

assay and purity of lyoproduct - measured after compounding, freeze drying and reconstitution to 5 mL

| | Lyo stability HpßCD t = 0 | HpßCD t = 1.5 months at 25° C. | SBECD t = 0 | SBECD t = 1.5 months at 25° C. | HpßCD t = 0 | HpßCD t = 1.5 months at 25° C. | SBECD t = 0 | SBECD t = 1.5 months at 25° C. |
|---|---|---|---|---|---|---|---|---|
| target pH | pH 7.4 | PH 7.4 | pH 7.4 | pH 7.4 | pH 7.8 | pH 7.8 | pH 7.8 | pH 7.8 |
| | mg | mg | mg | mg | mg | mg | mg | mg |
| Levosimendan | 12.5 | 12.5 | 12.5 | 12.5 | 12.5 | 12.5 | 12.5 | 12.5 |
| Hpßcd/SBECD | 875 | 875 | 875 | 875 | 875 | 875 | 875 | 875 |
| WFI ad mL | 5 | 5 | 5 | 5 | 5 | 5 | 5 | 5 |
| Assay mg/mL | 2.35 | 2.16 | 2.46 | 2.49 | 2.36 | 2.17 | 2.50 | 2.49 |
| Impurity µg/mL | | | | | | | | |
| Levosimendan 01 | | | | | | | | |
| RRT 0.32 | RRT 0.32: 43.3 | RRT 0.32: 240.5 | n.d. | n.d. | RRT 0.32: 50.1 | RRT 0.32: 227.3 | n.d. | n.d. |
| RRT 0.79 | | | | | | | | |
| RRT0.81 | | RRT 0.79: 197.7 | | | | RRT 0.79: 197.9 | | |
| RRT 0.95 | | | | | | | | |
| LC-ESI-(+) MS | | | | | | | | |

| Levosimendan 01 | known | m/z 204 |
|---|---|---|
| RRT 0.32 | not known | m/z 298 amu, 336 amu |
| RRT 0.79 | not known | m/z 443 amu |
| RRT 0.81 | OR-1420 | monohydrolyzed impurity m/z = 299 (M + 1) Mono-hydrolized impurity |
| RRT 0.95 | not known | no m/z so far | learnings
1) SBECD is much more stable-see impurity testing
2) HPßCD less stable-as can be taken from assay decrease and impurity (degradation product) build up

TABLE 3

SBECD-Levo form +40° C. ± 2° C./75% RH ± 5%) all values rounded to one digit after the comma

| Test Description | Limit | T = 0 | T = 1 week | T = 2 weeks | T = 1 month | T = 2 months | T = 3 months |
|---|---|---|---|---|---|---|---|
| Appearance of the lyo cake | No shrinkage | No shrinkage | No shrinkage | No shrinkage | No shrinkage | No shrinkage | No shrinkage |
| Reconstitution time | <2 min | 18 sec | 21 sec | 25 sec | 23 sec | 22 sec | 23 sec |
| Clarity of reconstituted solution | clear solution - after nmt 10 min at room temperature ≤10 NTU | clear yellowish solution 0.8 | clear yellowish solution 0.3 | clear yellowish solution 0.6 | clear yellowish solution 0.4 | clear yellowish solution 0.7 | clear orange-yellowish solution 0.4 |
| Color of solution (C*), tristimulus USP [1061] | determine and report | 120.7 | 121.0 | 121.6 | 121.4 | 121.8 | 122.5 |
| Identity/Assay (mg/mL) | retention time conform to standards determine and report | 2.3 | 2.3 | 2.4 | 2.4 | 2.3 | 2.3 |
| Purity (µg/mL), LC-ESI(+)-MS Impurities RRT obtained from various stability studies | Levosimendan/01/ m/z 204 amu (OR-1855) | n.d. | n.d. | n.d. | n.d. | n.d. | n.d. |
| | RRT 0.34 m/z 298.334 amu | n.d. | n.d. | n.d. | n.d. | n.d. | n.d. |
| | RRT 0.53, m/z 356 | n.d. | n.d. | n.d. | n.d. | n.d. | n.d. |
| | RRT 0.76 m/z 443 amu | n.d. | n.d. | n.d. | n.d. | n.d. | n.d. |
| | RRT 0.81 monohydrolyzed impurity OR-1420, m/z | n.d. | n.d. | n.d. | n.d. | n.d. | n.d. |

TABLE 3-continued

SBECD-Levo form +40° C. ± 2° C./75% RH ± 5%) all values rounded to one digit after the comma

| Test Description | Limit | T = 0 | T = 1 week | T = 2 weeks | T = 1 month | T = 2 months | T = 3 months |
|---|---|---|---|---|---|---|---|
| | RRT 0.90 (presumably dihydrolized impurity) | n.d. | n.d. | n.d. | n.d. | n.d. | n.d. |
| | RRT 0.95, not known yet | 6.2 | 0.9 | 11.4 | 5.9 | 5.9 | 9.8 |
| | RRT 1.08, not known yet | n.d. | n.d. | n.d. | n.d. | n.d. | n.d. |

TABLE 4

SBECD-Levo form +5° C. ± 3° C. all values rounded to one digit after the comma

| Test Description | Limit | T = 0 | T = 1 week | T = 2 weeks | T = 1 month | T = 2 months | T = 3 months |
|---|---|---|---|---|---|---|---|
| Appearance of the lyo cake | No shrinkage | No shrinkage | No shrinkage | No shrinkage | No shrinkage | No shrinkage | No shrinkage |
| Reconstitution time | <2 min | 18 sec | 20 sec | 25 sec | 24 sec | 21 sec | 25 sec |
| Clarity of reconstituted solution | clear solution - after nmt 10 min at room temperature ≤10 NTU | clear yellowish solution 0.8 | clear yellowish solution 0.6 | clear yellowish solution 0.6 | clear yellowish solution 0.5 | clear yellowish solution 1.0 | clear orange-yellowish solution 0.6 |
| Color of solution (C*); tristimulus USP [1061] | determine and report | 120.7 | 120.8 | 121.2 | 121.0 | 121.2 | 121.8 |
| Identity/Assay (mg/mL) | retention time conform to standards, determine and report | 2.3 | 2.3 | 2.3 | 2.4 | 2.3 | 2.4 |
| Purity (μg/mL) LC-ESI(+)-MS Impurities RRT obtained from various stability studies | Levosimendan/01/m/z 204 amu (OR-1855) | n.d. | n.d. | n.d. | n.d. | n.d. | n.d. |
| | RRT 0.34 m/z 298.334 amu | n.d. | n.d. | n.d. | n.d. | n.d. | n.d. |
| | RRT 0.53, m/z 356 | n.d. | n.d. | n.d. | n.d. | n.d. | n.d. |
| | RRT 0.76 m/z 443 amu | n.d. | n.d. | n.d. | n.d. | n.d. | n.d. |
| | RRT 0.81 monohydrolyzed impurity OR-1420, m/z 299 | n.d. | n.d. | n.d. | n.d. | n.d. | n.d. |
| | RRT 0.90 (presumably dihydrolized impurity) | n.d. | n.d. | n.d. | n.d. | n.d. | n.d. |
| | RRT 0.95, not known yet | 6.2 | n.d. | 11.0 | 3.6 | 5.3 | 9.8 |
| | RRT 1.08, not known yet | n.d. | n.d. | n.d. | n.d. | n.d. | n.d. |

What is claimed is:

1. A pharmaceutical composition, comprising Levosimendan as active ingredient, and sulfo-butyl-ether beta-cyclodextrin as a solubilizer, with the proviso that the use of co-solvents comprised of ethanol, propyleneglycol, polyethyleneglycol, poloxamers or polyvinylpyrrolidon is excluded.

2. The pharmaceutical composition according to claim 1, wherein Levosimendan is present in solubilized form.

3. The pharmaceutical composition according to claim 2, wherein Levosimendan is solubilized by micellarization or by complexation.

4. The pharmaceutical composition according to claim 1, which is in the form of a solution.

5. The pharmaceutical composition according to claim 4, wherein the amount of the solubilizer is 2 to 45 percent by weight of the pharmaceutical composition.

6. The pharmaceutical composition according to claim 4, wherein the pH of the solution is in the range of 7.0 to 8.0.

7. The pharmaceutical composition according to claim 6, wherein the pH of the solution is in the range of 7.2 to 7.8.

8. The pharmaceutical composition according to claim 4, which is in the form of an aqueous solution.

9. The pharmaceutical composition according to claim 1, which is a solution suitable for an intravenous application.

10. The pharmaceutical composition according to claim 1, comprising the Levosimendan in an amount of 1 to 15 mg/ml solution.

11. A dried powder obtainable from a pharmaceutical composition according to claim 1, wherein the dried powder is obtainable by drying a solution comprising the solubilized Levosimendan.

12. A cried powder according to claim 11 for use as a medicament.

13. A dried powder according to claim 11 for use in a method of treating congestive heart failure or acutely decompensated heart failure (ADHF).

14. The dried powder for use according to claim 13, wherein for administration the dried powder is reconstituted to a solution suitable for intravenous administration.

15. The dried powder for use according to claim 14, which is an intravenous infusion concentrate comprising the Levosimendan in an amount of 1 to 15 mg/ml solution.

16. The dried powder for use according to claim 15, wherein the concentrate is to be adjusted to a pH in the range of 7.2 to 8.0.

17. The dried powder for use according to claim 13, wherein solvent for reconstitution is water, or an isotonic buffer system.

18. The dried powder for use according to claim 17, wherein the water has a pH in the range of 7.2 to 7.8, or the isotonic buffer system has a pH in the range of 7.2 to 7.4.

19. The dried powder according to claim 11, wherein the dried powder is obtainable by freeze-drying or spray-drying the solution comprising the solubilized Levosimendan.

20. The dried, powder according to claim 11, wherein the dried powder is obtainable by drying a solution comprising the solubilized Levosimendan and a suitable pharmaceutical vehicle used for freeze-drying.

21. A method for preparing a dried powder according to claim 11, comprising the steps of:
   providing a solution of the solubilizer in a solvent,
   adding the Levosimendan into that solution,
   sterilization of the thus obtained solution, and
   drying the sterilized solution.

22. The method according, to claim 21, wherein the solution of the solubilizer in a solvent is adjusted to a pH in the range of 4.0 to 8.0.

23. The method according to claim 21, wherein the sterilization comprises sterile filtration.

24. The method according to claim 21, wherein the method further comprises split charging the sterilized solution.

25. The method according to claim 21, wherein the drying comprises freeze-drying or spray-drying.

* * * * *